US00PP36472P2

(12) United States Plant Patent
Hartman

(10) Patent No.: US PP36,472 P2
(45) Date of Patent: Feb. 18, 2025

(54) ***CALADIUM* PLANT NAMED 'RSB Rd (BOM) 2319-279'**

(50) Latin Name: *Caladium X hortulanum*
Varietal Denomination: RSB Rd (BOM) 2319-279

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,770

(22) Filed: May 7, 2024

(51) Int. Cl.
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Caladium* plant named 'RSB Rd (BOM) 2319-279', characterized by its upright plant habit and intermediate to tall in height; moderately dense, leafy and bushy appearance; vigorous growth habit and rapid growth rate; fancy-type leaves with dark red-colored centers and venation surrounded by dark green-colored marginal areas with variable and random yellowish white-colored speckles; and petioles that are tannish pink in color with dark greenish brown-colored markings.

4 Drawing Sheets

Figure 1:
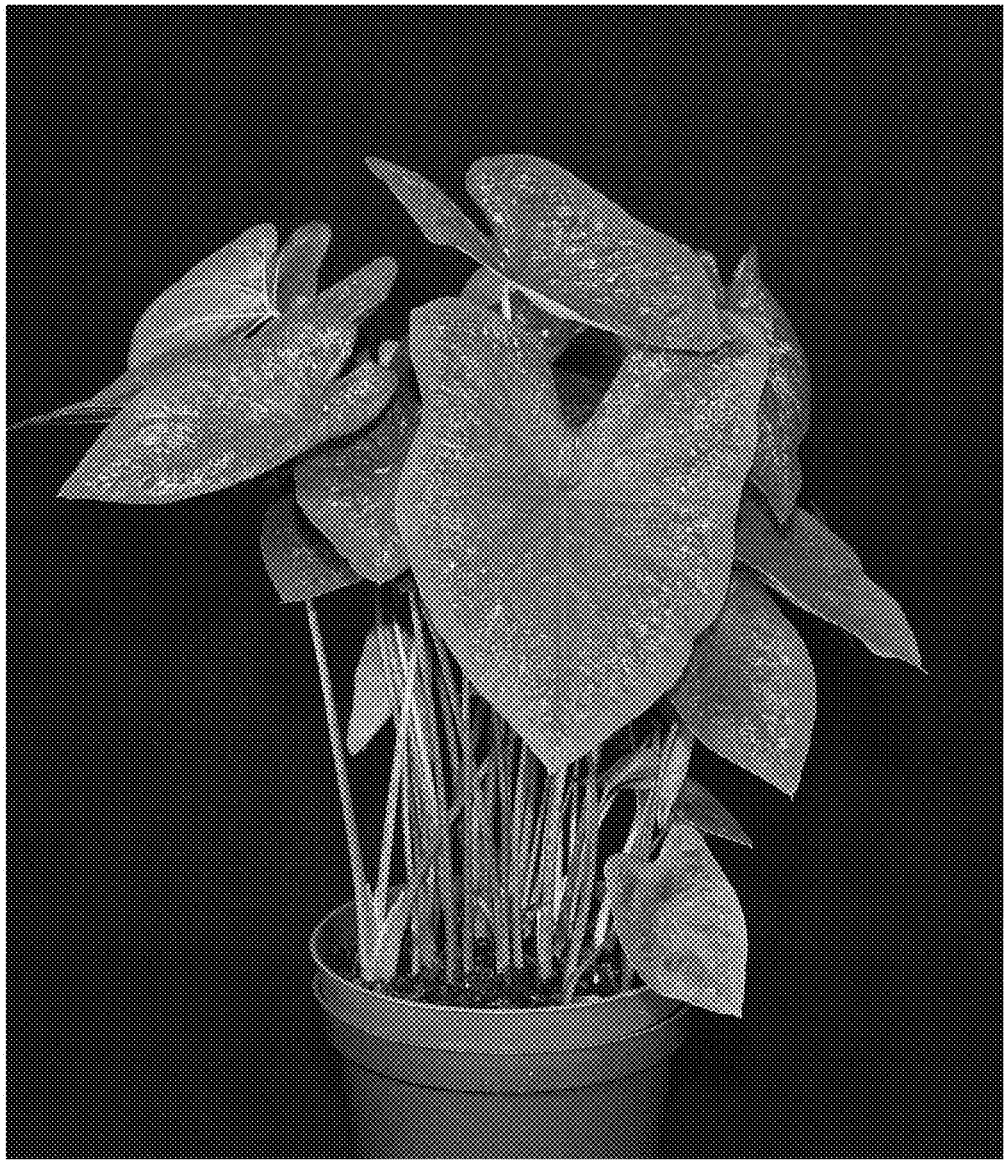

Botanical designation: *Caladium* X *hortulanum*.
Cultivar denomination: 'RSB Rd (BOM) 2319-279'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'RSB Rd (BOM) 2319-279'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April 2011 in Avon Park, Florida of *Caladium* X *hortulanum* 'White Delight', disclosed in U.S. Plant Pat. No. 21,216, as the female, or seed, parent with *Caladium* X *hortulanum* 'RFL 2317-114', disclosed in U.S. Plant Pat. No. 27,964, as the male, or pollen, parent. The new *Caladium* plant was discovered and selected by the Inventor as a single plant within the progeny of the stated cross-pollination in a controlled outdoor nursery environment in Avon Park, Florida in September 2012.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April 2013 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RSB Rd (BOM) 2319-279'. These characteristics in combination distinguish 'RSB Rd (BOM) 2319-279' as a new and distinct *Caladium* plant:

1. Upright plant habit and intermediate to tall in height; moderately dense, leafy and bushy appearance.
2. Vigorous growth habit and rapid growth rate.
3. Fancy-type leaves with dark red-colored centers and venation surrounded by dark green-colored marginal areas with variable and random yellowish white-colored speckles.
4. Petioles that are tannish pink in color with dark greenish brown-colored markings.

Plants of the new *Caladium* differ primarily from plants of the female parent, 'White Delight', in the following characteristics:

1. Leaves of plants of the new *Caladium* are fancy types whereas leaves of plants of 'White Delight' are lance-types.
2. Leaves of plants of the new *Caladium* have dark red-colored centers and venation surrounded by dark green-colored marginal areas with variable and random yellowish white-colored speckles whereas leaves of plants of 'White Delight' are white to grey-green in color with white-colored main veins and dark green-colored borders.
3. Petioles of plants of the new *Caladium* are tannish pink in color with dark greenish brown-colored markings whereas petioles of plants of 'White Delight' are dark greenish brown with dark brown-colored stippling and tessellations.

Plants of the new *Caladium* differ primarily from plants of the male parent, 'RFL 2317-114', in the following characteristics:

1. Plants of the new *Caladium* are not as dense as plants of 'RFL 2317-114'.
2. Leaves of plants of the new *Caladium* have dark red-colored centers and venation surrounded by dark green-colored marginal areas with variable and random yellowish white-colored speckles whereas leaves of plants of 'RFL 2317-114' are dark green in color with red-colored venation, bright red-colored areas surrounding the veins and salmon pink-colored spots.
3. Petioles of plants of the new *Caladium* are tannish pink in color with dark greenish brown-colored markings whereas petioles of plants of 'RFL 2317-114' are reddish pink in color with proximal brownish green-colored markings.

Plants of the new *Caladium* can be compared to plants of *Caladium* X *hortulanum* 'Bombshell', disclosed in U.S. Plant Pat. No. 23,817. In side-by-side comparisons, plants of the new *Caladium* differ primarily from plants of 'Bombshell' in the following characteristics:

1. Plants of the new *Caladium* are more mounding than plants of 'Bombshell'.
2. Leaves of plants of the new *Caladium* have dark red-colored centers and venation surrounded by dark green-colored marginal areas with variable and random yellowish white-colored speckles whereas leaves of plants of 'Bombshell' are dark red to greyed purple-colored interveinal areas and venation surrounded with dark green-colored borders.
3. Petioles of plants of the new *Caladium* are tannish pink in color with dark greenish brown-colored markings whereas petioles of plants of 'Bombshell' are tannish pink in color with almost black-colored markings.

Plants of the new *Caladium* can also be compared to plants of *Caladium* X *hortulanum* 'Postman Joyner', not patented. In side-by-side comparisons, plants of the new *Caladium* differ primarily from plants of 'Postman Joyner' in the following characteristics:

1. Plants of the new *Caladium* are shorter and more mounding than plants of 'Postman Joyner'.
2. Leaves of plants of the new *Caladium* have dark red-colored centers and venation surrounded by dark green-colored marginal areas with variable and random yellowish white-colored speckles whereas leaves of plants of 'Postman Joyner' are dark green in color with bright red-colored centers.
3. Petioles of plants of the new *Caladium* are tannish pink in color with dark greenish brown-colored markings whereas petioles of plants of 'Postman Joyner' are close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'RSB Rd (BOM) 2319-279' grown in a container that has had its tuber de-eyed prior to planting.

Figure 2:
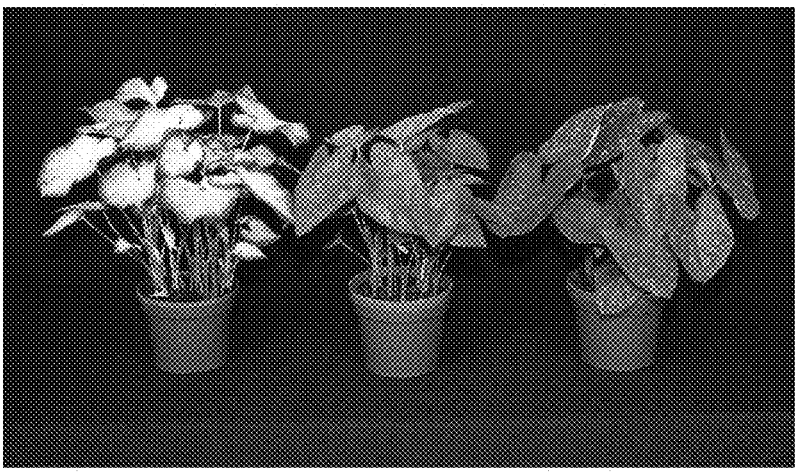

The photograph at the top of the second sheet (FIG. 2) is side perspective view of typical plants of the female parent, 'White Delight' (left), 'RSB Rd (BOM) 2319-279' (center) and the male parent, 'RFL 2317-114' (right).

Figure 3:
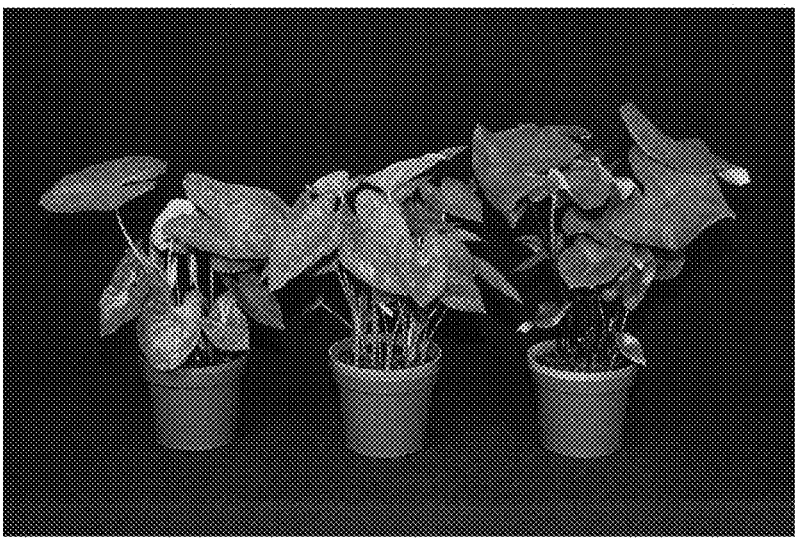

The photograph at the bottom of the second sheet (FIG. 3) is side perspective view of typical plants of 'Bombshell' (left), 'RSB Rd (BOM) 2319-279' (center) and 'Postman Joyner' (right).

Figure 4:
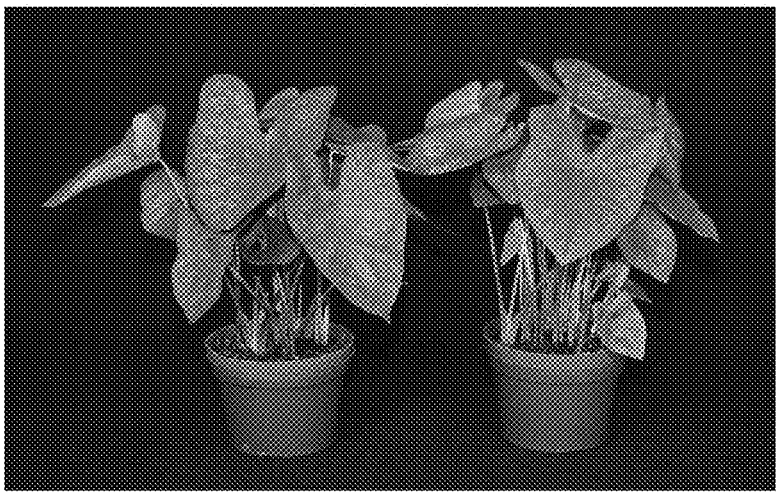

The photograph at the top of the third sheet (FIG. 4) is a comparison view of typical plants of 'RSB Rd (BOM) 2319-279' grown in containers, the plant on the left has not had its tuber de-eyed and the plant on the right has had its tuber de-eyed prior to planting.

Figure 5:
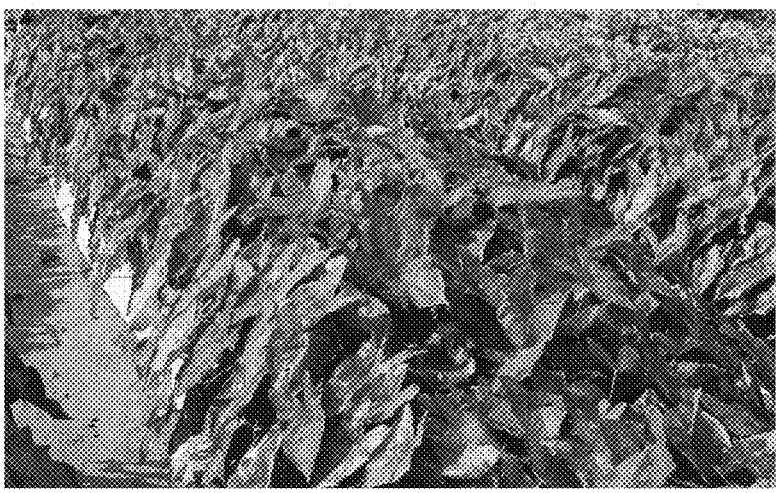

The photograph at the bottom of the third sheet (FIG. 5) is a side perspective view of typical plants of 'RSB Rd (BOM) 2319-279' grown in an open production field.

Figure 6:
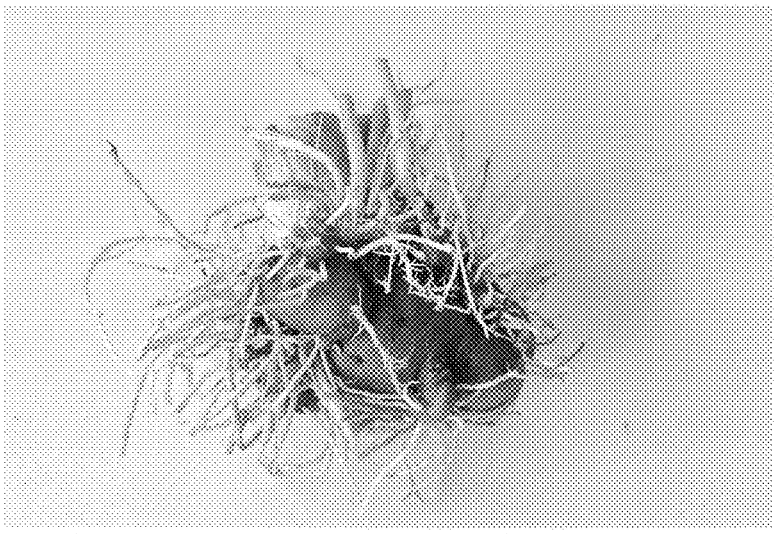

The photograph at the top of the fourth sheet (FIG. 6) is a close-up view of typical freshly-harvested tubers with roots and leaf petioles of 'RSB Rd (BOM) 2319-279'.

Figure 7:
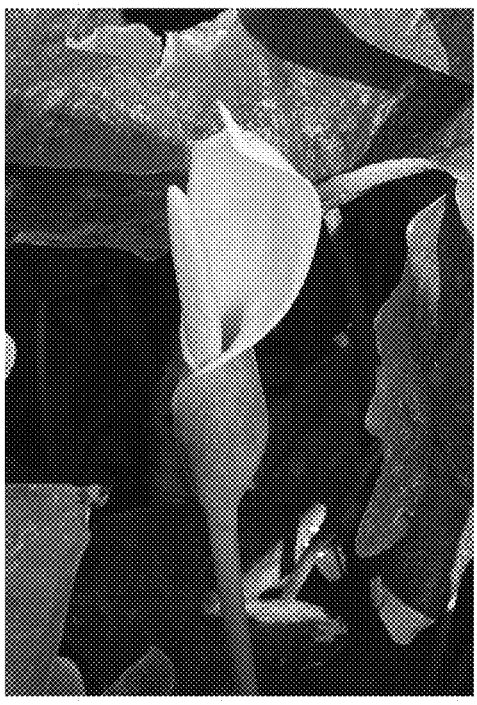

The photograph at the bottom of the fourth sheet (FIG. 7) is a close-up view of a typical inflorescence of 'RSB Rd (BOM) 2319-279'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were five to six weeks old and plants grown in the outdoor nursery were seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'RSB Rd (BOM) 2319-279'.

Parentage:

*Female, or seed, parent.*—*Caladium* X *hortulanum* 'White Delight', disclosed in U.S. Plant Pat. No. 21,216.

*Male, or pollen, parent.*—*Caladium* X *hortulanum* 'RFL 2317-114', disclosed in U.S. Plant Pat. No. 27,964.

PROPAGATION:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and branched; individual segments are elliptic to ovate or irregular in shape. Height: About 3.2 cm to 3.4 cm. Diameter: About 5.7 cm to 7.8 cm. Segment height: About 2.5 cm to 2.9 cm. Segment diameter: About 2.9 cm to 3 cm. Axillary bud shape: Roughly triangular. Axillary bud height: About 5 mm. Axillary bud width: About 5 mm. Texture: Thick, starchy; somewhat brittle. Color: Periderm, freshly-harvested: Close to 174A, 174D and/or 177A. Periderm, dried: Close to 200A. Epidermis: Close to 179C tinged with close to 180D. Cortical tissue: Close to 11C. Axillary buds: Close to 49A to 49B. Root description: Moderately thick, fleshy contractile roots with moderate branching; color, close to N155D tinged with close to 49B; actual color of the roots is dependent on substrate composition, water quality, fertilizer type and formulation, substrate temperature and physiological age of roots; root density, moderately dense.

Plant description:

*Plant type*.—Herbaceous perennial; suitable as a potted plant in containers 15-cm to 25-cm and suitable as a landscape plant in shaded areas.

*Plant and growth habit*.—Upright plant habit; intermediate to tall in height; moderately dense, leafy and bushy appearance; vigorous growth habit and rapid growth rate; potted plants finish in saleable form in about five to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 24 cm to 27 cm.

*Plant height, from soil level to top of foliar plane, shade house-grown potted plants, tubers not de-eyed*.—About 35 cm to 40 cm.

*Plant height, from soil level to top of floral plane, shade house-grown potted plants, tubers de-eyed and not de-eyed*.—About 36 cm.

*Plant diameter, shade house-grown potted plants, tubers de-eyed*.—About 29 cm to 37 cm.

*Plant diameter, shade house-grown potted plants, tubers not de-eyed*.—About 26 cm to 38 cm.

*Number of shoots per plant, shade house-grown potted plants, tubers de-eyed*.—About six to ten develop per #1 tuber.

*Number of shoots per plant, shade house-grown potted plants, tubers not de-eyed*.—About two to five develop per #1 tuber.

*Cataphylls, shade house-grown potted plants*.—Length: About 5.5 cm to 9 cm. Width: About 1.1 cm. Shape: Lanceolate to deltoid. Apex: Acute or acuminate. Base: Sheathing the stem. Texture, outer and inner surfaces: Smooth, glabrous. Color, outer surface: Close to NN155C and N170D, densely and variably streaked and stippled with close to 200B and tinged with close to 147B; color becoming closer to N199C with subsequent development. Color, inner surface: Close to N155C to N155D; colors and color patterns may be visible from outer surface visible.

Leaf description:

*Arrangement and type*.—Alternate; simple; fancy-type.

*Length, shade house-grown potted plants, tubers de-eyed*.—About 14 cm to 15 cm.

*Length, shade house-grown potted plants, tubers not de-eyed*.—About 16.5 cm to 17 cm.

*Width, shade house-grown potted plants, tubers de-eyed*.—About 7.3 cm to 10.9 cm.

*Width, shade house-grown potted plants, tubers not de-eyed*.—About 10.6 cm to 16 cm.

*Shape*.—Broadly ovate with cordate tendencies.

*Apex*.—Acuminate to acute.

*Base*.—Sagittate to peltate, cordate.

*Margin*.—Entire; mostly flat with broad undulations.

*Texture and luster, upper surface*.—Smooth, glabrous; dull sheen.

*Texture and luster, lower surface*.—Smooth, glabrous; glaucous close to veins; dull sheen.

*Venation pattern*.—Pinnate and palmate.

*Color, shade house-grown potted plants*.—When developing and fully expanded leaves, upper surface: Centers: Close to 185A, 46A, NN137A, 183A and/or 181D; variable and random speckles, close to 158B to 158C. Marginal areas: Close to NN137A; variable and random flecks, close to 145D; edges, close to 187A. Basal notch: Close to 187A and 185A. Main vein: Close to 46A and N45C; areas adjacent to the main vein, close to N45D, 46A and 185A. Lateral venation: Close to 46A; areas adjacent to the lateral venation, close to 185A and 46A. When developing and fully expanded leaves, lower surface: Centers: Close to 183B to 183C, 191A and/or N170D; variable and random speckles, close to 158C. Marginal areas: Close to 191A; edges, close to 187A. Basal notch: Close to 187A. Main vein: Close to 182C and 185B to 185C; areas adjacent to the main vein, close to 183B to 183C. Lateral venation: Close to 182D and 197B; areas adjacent to the lateral venation, close to 183B to 183C.

*Petioles*.—Aspect: Initially upright and straight and leaning outwardly with development; flexible. Length, shade house-grown potted plants, tubers de-eyed: About 18 cm to 22.5 cm. Length, shade house-grown potted plants, tubers not de- eyed: About 22 cm to 30.1 cm. Diameter, distally, shade house-grown potted plants, tubers de-eyed: About 2.5 mm to 3 mm. Diameter, proximally, shade house-grown potted plants, tubers de-eyed: About 4 mm to 6 mm. Diameter, distally, shade house-grown potted plants, tubers not de-eyed: About 3.5 mm to 4 mm. Diameter, proximally, shade house-grown potted plants, tubers not de-eyed: About 5 mm to 7 mm. Texture: Smooth, glabrous; glaucous. Color, shade house-grown potted plants: Close to 181D with streaks, stippling and tessellations, close to N189A and N200A; just below the leaf junction, close to 181A and 185C to 185D. Wing length, shade house-grown potted plants: About 4 cm to 8 cm. Wing diameter, shade house-grown potted plants: About 6 mm to 8 mm. Texture and luster, inner and outer surfaces: Smooth, glabrous; dull to slightly glossy. Wing color, shade house-grown potted plants: Outer surface: Close to N155B densely and variably streaked, stippled and speckled with close to N189A and N200A. Inner surface: Close to N155B; colors and patterns from the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers. Fragrance: Night-fragrant; jasmine-like with camphor note.

*Natural flowering season and flower longevity*.—Plants of the new *Caladium* typically flower during the spring in central Florida; flowers develop about six weeks after growth commences; inflorescences last about three days before fading; inflorescences persistent.

*Spathe*.—Length, overall: About 11 cm. Length, distal open portion: About 6.2 cm. Length, proximal closed portion: About 4.8 cm. Width, distal open portion: About 4.2 cm. Depth, distal open portion: About 2.3 cm. Width, at constriction: About 1.4 cm to 1.6 cm. Width, proximal closed portion: About 2.7 cm to 3 cm. Shape, open portion: Ovate to elliptic. Apex: Acute to acuminate. Base: Acute. Margin: Entire. Texture and luster, front surface: Smooth, glabrous; dull sheen. Texture and luster, rear surface: Smooth, glabrous; distally, dull and proximally, slightly glaucous. Color, front surface: Distal open portion: Close to N155A to N155C; with subsequent development, distally becoming closer to 199B. Proximal closed portion: Close to 148C, distally, flushed with close to 187A; color does not change with subsequent development. Color, rear surface: Distal open portion: Close to 145C, 145D and 155C; color does not change with subsequent development. Proximal closed portion: Close to 159C and 160D with variable areas of close to 147D and streaks and areas flushed with close to 183D and 182C to 182D; color does not change with subsequent development.

*Spadix*.—Length, overall: About 7 cm. Length, male flower zone: About 4.5 cm. Length, sterile zone: About 2 cm. Length, female flower zone: About 2.5 cm. Diameter, male flower zone: About 7 mm. Diameter, sterile flower zone: About 5.5 mm. Diameter, female flower zone: About 8.5 mm. Shape: Columnar, spindle-shaped. Apex: Obtuse, rounded. Base: Obtuse. Aspect: Upright. Color, mature, male zone: Close to 159D. Color, mature, sterile zone: Close to 159D. Color, mature, female zone: Stigmas, close to 158C; ovaries, close to N155C. Male flowers: Quantity per spadix: About 75. Shape: Obovate. Height: About 3 mm. Diameter: About 3 mm. Pollen amount: Abundant. Pollen color: Close to 8D. Female flowers: Quantity per spadix: About 140. Shape: Obovate. Height: About 3 mm. Diameter: About 2 mm. Stigma color: Close to 158C. Ovary color: Close to N155C.

*Scapes*.—Length: About 25 cm. Diameter: About 6 mm. Strength: Sturdy; flexible. Aspect: Mostly erect, straight. Texture and luster: Smooth, glabrous; glaucous and dull. Color: Close to 147A tinged with close to N199A and streaked, stippled and tessellated with close to N200A; just below spathe, close to 147C and flushed with close to 200B to 200C.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RSB Rd (BOM) 2319-279' as illustrated and described herein.

* * * * *